United States Patent [19]

Steiner et al.

[11] Patent Number: 5,447,542
[45] Date of Patent: Sep. 5, 1995

[54] PROCESS FOR SEPARATING AND PURIFYING SUBSTANCES BY CRYSTALLIZATION FROM THE MELT

[75] Inventors: Rudolf Steiner, Erlangen; Axel König, Stuttgart; Siegbert Rittner, Mörfelden, all of Germany

[73] Assignee: Hoechst Aktiengesellschaft, Frankfurt, Germany

[21] Appl. No.: 230,498

[22] Filed: Apr. 20, 1994

[30] Foreign Application Priority Data

Apr. 22, 1993 [DE] Germany .................. 43 13 121.2

[51] Int. Cl.⁶ .................. B01D 9/00; C07C 7/14; C10G 21/00
[52] U.S. Cl. .................. 23/296; 585/816; 208/319; 23/308 R
[58] Field of Search .................. 585/816, 817; 23/296, 23/308 R; 208/319; 62/58

[56] References Cited

U.S. PATENT DOCUMENTS 3,592,016  7/1971  Blight ........................ 62/58

FOREIGN PATENT DOCUMENTS 2135539 12/1972 Germany .
2158754  6/1973 Germany .

OTHER PUBLICATIONS

Patent Abstracts of Japan, vol. 13, No. 336 (C-623) (3684), Jul. 27, 1989, Abstract No. 1-115404 which relates to DE 21 35 539.

German Abstract No. 2158754 which relates to DE 21 58 754.

*Primary Examiner*—Gary P. Straub
*Attorney, Agent, or Firm*—Curtis, Morris & Safford

[57] ABSTRACT

In the process for separating and purifying substances by crystallization from the melt under pressure, the melt is subjected to pressure under an inert gas atmosphere and then cooled, whereupon it crystallizes. The residual melt is separated from the resulting crystals, after which the crystals are degassed by reducing the pressure and are caused to sweat, and the sweat oil is separated off.

3 Claims, No Drawings

PROCESS FOR SEPARATING AND PURIFYING SUBSTANCES BY CRYSTALLIZATION FROM THE MELT

The invention relates to a process for separating and purifying substances by crystallization from the melt under pressure.

Crystallization from the melt is understood as meaning the separation and/or purification of substances where one or more components crystallize out of a melt and are separated off while other components remain in the non-solidified part of the melt, so-called residual melt.

Crystallization from the melt is known. The melt is cooled at atmospheric pressure and crystallizes. The residual melt is separated off from the crystals. The crystals are then heated again until they sweat and the sweat oil (drip oil) separates off.

In another process, the melt is subjected to pressure by a press ram and then crystallized by lowering the temperature while maintaining the pressure. After removal of the residual melt, the sweating process is initiated by lowering the pressure. In this process, small, poorly formed crystals which make solid-liquid separation more difficult are disadvantageous. The invention intends to provide a remedy here.

The object is achieved by a process of the type stated at the outset, in which
a) an inert gas is introduced into the melt,
b) the melt is subjected to pressure under an inert gas atmosphere and is then cooled, whereupon it crystalizes at pressures of 100 to 5,000 bar,
c) the residual melt is separated off from the resulting crystals,
d) the crystals are then degassed by lowering the pressure and are caused to sweat and
e) the sweat oil is separated off.

The gas pressure can be increased gradually to the final pressure and lowered gradually after the residual melt has been separated off. Suitable inert gases are in particular those which are soluble in the particular melt. For example, nitrogen, carbon dioxide, ethane, ethene, propane, etc. or mixtures thereof are suitable for the naphthalene/biphenyl and p-/m-dichlorobenzene systems. In order to achieve better solubility, the gas can be distributed in the melt via nozzles and the like while moving the melt. The melt can be crystallized at pressures of 100 to 5,000 bar with corresponding temperature reduction. The required pressure depends on the material system and on the composition of the components.

The advantages of the process are to be seen essentially in the degassing of the crystals, by means of which the crystals are loosened up, effectively improving the sweating process. The gradual pressure relief allows sweat oils having different degrees of contamination to separate off.

The invention is illustrated in detail below with reference to Examples:

EXAMPLE 1

A test tube was freely suspended in an autoclave having a capacity of 1.5 l, provided with 2 opposite slot-like inspection windows and designed for a maximum operating pressure of 300 bar and an operating temperature of 250° C. About 10 g of a mixture of 66% by weight of naphthalene and 34% by weight of biphenyl were introduced into the test tube, said mixture being present in molten form in a nitrogen atmosphere at a pressure of 150 bar and at temperatures above 61° C. The temperature was measured using a thermocouple close to the sample to be investigated. Temperature regulation was effected via the heating of the autoclave by means of a liquid thermostat. On cooling, the first crystals appeared at 60.4° C. and crystals accounted for about 1/6 of the volume at 59.8° C. and about 9/10 of the volume at 58.3° C. At 54° C., the total melt was "solid" i.e. no residual melt was detectable. The pressure was then gradually reduced. At about 100 bar, the first gas bubbles appeared, the crystals became opaque at 65 bar and a liquid phase formed at 30 bar, the temperature having decreased to 49.5° C. in the meantime. At 1 bar and 38.7° C., the liquid layer finally filled about 1/5 of the test tube volume. The residual melt slowly began to crystallize on further cooling, but not until below 38° C. The analysis showed substantial differences in the composition of the two phases: the crystals contained about 75% by weight of naphthalene and the separated residual melt about 46% by weight of naphthalene.

A reference experiment carried out at atmospheric pressure showed that the crystallization of the starting melt begins at 57.0° C. and the residual melt can no longer be separated off after cooling to a temperature below 50° C.

EXAMPLE 2

An autoclave having a capacity of 0.2 l and an internally arranged heat exchanger plate was mounted on a stand so that it could be rotated about the stand axis during the experiment. It has an electrically heatable heating jacket, and the heat exchanger plate is provided with a liquid thermostat. At the crystallization position, the heat exchanger plate is in the lower part and is surrounded by melt. After the end of the crystallization, the autoclave is tilted so that the plate enters the upper part, allowing the residual melt and the sweat oil fraction to run off. 50 g of a mixture of 70% by weight of naphthalene and 30% by weight of biphenyl were introduced into the autoclave, and the heat exchanger was immersed in the mixture present in the lower part of the autoclave. In the autoclave under a nitrogen atmosphere, the pressure was adjusted to 100 bar and the autoclave content was heated to 75° C. The heat exchanger plate was regulated at the same temperature. Under these conditions, the melt was heated for one hour and saturated with gas while moving the autoclave. The temperature of the heat exchanger was then reduced to 50° C. and, one hour later, the autoclave temperature was also reduced to this value. After a further hour, the apparatus was rotated so that the heat exchanger plate was now present at the top and the residual melt could run off. The pressure was then reduced to atmospheric pressure at intervals of 10 bar per 5 minutes, in order to remove occluded portions of the residual melt and sweat oil from the crystalline system. The autoclave was then cooled to room temperature.

The heat exchanger plate was surrounded by crystals whose average composition contained about 83% by weight of naphthalene. The naphthalene content in the interior of the layer of crystals was up to 89% by weight and hence substantially higher than in the outer layer with about 73% by weight. A layer of residual melt which contained about 50% by weight of naphthalene had collected at the bottom of the autoclave.

In contrast, in a reference experiment at atmospheric pressure, no residual melt collected at the bottom of the pressure vessel.

EXAMPLE 3

68 g of a mixture of 88% by weight of p-dichlorobenzene and 12% by weight of m-dichlorobenzene were introduced into the autoclave having the heat exchanger plate according to Example 2. This mixture was subjected to a pressure of 100 bar at 65° C. under a nitrogen atmosphere. The crystallization began at 40° C. and ended at 30° C. After the subsequent pressure relief, about 48 g of crystals having a purity of 99.95% by weight of p-dichlorobenzene were obtained, while the residual melt contained about 62% by weight of p-dichlorobenzene.

Two reference experiments at atmospheric pressure gave crystals having purities of 99.41% by weight and 99.63% by weight. The purities of the crystals in the procedure with pressure relief were virtually a power of 10 higher than the purities in the reference experiments at atmospheric pressure.

EXAMPLE 4

In a further experiment, in this case with an inorganic substance, which was likewise carried out in the autoclave with the heat exchanger plate, 60 g of a mixture which consisted of 94% of phosphorous acid and 6% of various straight-chain fatty acids having a carbon chain length of $C_{12}$ to $C_{16}$ have been used. This mixture was crystallized under a nitrogen stream at 50 bar. The initial temperature was 69° C. (melt), and crystallization began at 60° C. and ended at 40° C. After the subsequent pressure relief, 44 g of crystals having a purity of 99.6% of phosphorous acid were obtained. A reference experiment at atmospheric pressure also resulted in separation into the crystals and residual melt, but the purity of the crystals was 97.7% and hence substantially lower than in the experiment under pressure with subsequent degassing.

We claim:

1. A process for separating and purifying substances by crystallization from the melt under pressure, wherein
   a) an inert gas is introduced into the melt at a pressure of 100 to 5,000 bar,
   b) the melt is then cooled, whereupon it crystallizes at a pressure of 100 to 5,000 bar,
   c) the residual melt is separated from the resulting crystals,
   d) the crystals are then degassed by lowering the pressure and are caused to sweat and
   e) the sweat oil (drip oil) is separated off.

2. The process as claimed in claim 1, wherein the melt is subjected to pressure under a nitrogen, carbon dioxide, ethane, ethene or propane atmosphere or an atmosphere comprising a mixture thereof.

3. The process as claimed in claim 1, wherein the inert gas is introduced into the melt via nozzles while simultaneously moving the melt.

* * * * *